United States Patent [19]
Trkovnik et al.

[11] Patent Number: 5,840,922
[45] Date of Patent: Nov. 24, 1998

[54] COUMARIN DERIVATIVES, AND PROCESSES FOR THEIR PREPARATION

[75] Inventors: Mladen Trkovnik; Zrinka Ivezić; Ljerka Polak, all of Zagreb, Croatia

[73] Assignee: PLIVA, farmaceutska, kemijska, prehrambena i kozmeticka industrija, dionicko drustvo, Zagreb, Croatia

[21] Appl. No.: 887,217

[22] Filed: Jul. 2, 1997

[30] Foreign Application Priority Data

Jul. 2, 1996 [HR] Croatia ................................ P960308A

[51] Int. Cl.⁶ ........................ C07D 311/12; C07D 311/16
[52] U.S. Cl. ............................................ 549/285; 549/288
[58] Field of Search ...................... 549/285, 288

[56] References Cited

U.S. PATENT DOCUMENTS 3,313,818  4/1967  Lesher ..................................... 549/288
4,210,758  7/1980  Connor .................................... 549/288

*Primary Examiner*—Bernard Dentz
*Attorney, Agent, or Firm*—Pollock, Vande Sande & Priddy

[57] ABSTRACT

The present invention relates to new coumarin derivatives represented by the general formula I

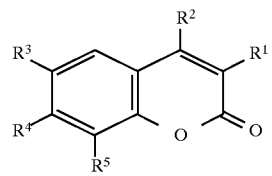

wherein $R^1=NH_2$ or $-NHCH=C(CO_2C_2H_5)_2$, $R^2=R^3=R^4=H$, $R^5=F$, $R^1=R^3=NHCH=C(CO_2C_2H_5)_2$, $R^2=R^4=R^5=H$, $R^1=H$ or $OH$, $R^3=NHCH=C(CO_2C_2H_5)_2$, $R^2=R^4=R^5=H$, $R^1=OH$, $R^2=R^3=R^4=H$, $R^5=-NHCH=C(CO_2C_2H_5)_2$, $R^1=R^3=R^5=H$, $R^2=CH_3$ or $CF_3$, $R^4=-NHCH=C(CO_2C_2H_5)_2$, processes for the preparation thereof and their use as intermediates for the synthesis of new coumarin derivatives with potential biological action.

9 Claims, No Drawings

COUMARIN DERIVATIVES, AND PROCESSES FOR THEIR PREPARATION

The present invention relates to new coumarin derivatives represented by the general formula I

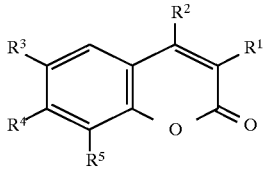

wherein $R^1=NH_2$ or $—NHCH=C(CO_2C_2H)_2$, $R^2=R^3=R^4=H$, $R^5=F$,
$R^1=R^3=NHCH=C(CO_2C_2H_5)_2$, $R^2=R^4=R^5=H$,
$R^1=H$ or $OH$, $R^3=NHCH=C(CO_2C_2H_5)_2$, $R^2=R^4R=H$,
$R^1=OH$, $R^2=R^3=R^4=H$, $R^5=—NHCH=C(CO_2C_2H_5)_2$,
$R^1=R^3=R^5=H$, $R^2=CH_3$ or $CF_3$, $R^4=—NHCH=C(C_2C_2H_5)_2$.

According to the present invention the new coumarin derivatives of the general formula I are prepared by reacting substituted coumarins of the formula II

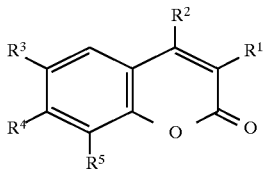

wherein $R^1=R^3=R^4=R^5=H$, $R^2=NH_2$,
$R^1=R^3=NH_2$, $R^2=R^4=R^5=H$,
$R^1=OH$, $R^2=R^4=R^5=H$, $R^3=NH_2$,
$R^1=OH$, $R^2=R^3=R^4=H$, $R^5=NH_2$,
$R^1=N_2$, $R^2=R^3=R^4=H$, $R^5=F$,
$R^1=R^3=R^5=H$, $R^2=CH_3$ or $CF_3$, $R^4=NH_2$, with diethyl-ethoxymethylene malonate of the formula III

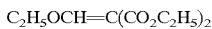

at the temperature of 120° C. within a period from 10 minutes to 27 hours, whereat coumarin malonate esters of the general formula I with the above defined substituents are obtained.

The starting substituted aminocoumarins of the general formula II, with the exception of the compound with $R^1=NH_2$, $R^2=R^3=R^4=H$, $R^5=F$, have already been described in the literature: F. W. Linch, J. Chem. Soc. 101 (1912) 1758; G. T. Morgan, F. M. G. Micklethwait, J. Chem. Soc. 85 (1904)1230; G. Kokotos, C. Tzougraki, J. Heterocyclic Chem. 23 (1986) 87; I. C. Ivanov, S. K. Karagiosov, I. Manolov, Arch. Pharm. (Weinheim) 324 (1991) 61.

New coumarin derivatives of the general formula I are useful intermediates for the synthesis of new coumarin derivatives with a potential biological action such as antimicrobial, antitumour and antiviral action.

The present process is illustrated but in no way limited by the following examples.

EXAMPLE 1

3-amino-8-fluorocoumarin

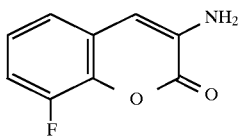

A solution of 3-acetylamino-8-fluorocoumarin (3.00 g, 0.014 mole) in concentrated sulfuric acid (2.65 g, 0.027 mole) was heated at 75°–80° C. for 1 hour. The cooled solution was poured onto an ice-water mixture and it was alkalized with a saturated $NaHCO_3$ water solution up to pH=6 and subsequently left to precipitate at +4° C. The obtained 3-amino-8-fluorocoumarin was recrystallized from 50% ethanol (1.63 g, 67%). M.p.: 173°–174° C.

Analysis:

calculated for $C_9H_6F_3NO_2$: C=60.34; H=3.38; N=7.82. found: C=59.97; H=3.22; N=7.72.

$^1$H-NMR (DMSO-$d_6$). δ/ppm: 5.9 (s, $NH_2$), 6.7 (s, H4); 7.1–7.2 (m, H5–H7). m/z: 178 (M$^-$), 151, 141, 134, 127.

EXAMPLE 2

Diethyl-{[(2-oxo-2H[1]-benzopyrano-6-yl)amino] methylene}malonate

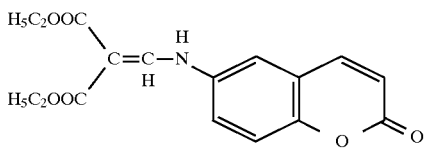

A solution of 6-aminocoumarin (2.00 g, 0.012 mole) in diethyl-etoxymethylene malonate (3.03 g, 0.014 mole) was heated for 10 minutes at 120° C., whereat a solidification of the reaction mixture occurred. The obtained light brown precipitate of diethyl-{[(2-oxo-2H[1]-benzopyrano-6-yl) amino]methylene}malonate (3.95 g, 96%) was recrystallized from ethanol. M.p.: 141°–142° C.

Analysis:

calculated for $C_{17}H_{17}NO_6$: C=61.62; H=5.17; N=4.23. found: C=61.87; H=4.99; N=4.17.

$^1$H-NMR (DMSO-$d_6$). δ/ppm: 1.3 (t, $CH_3$), 4.3 (q, $CH_2$); 6.6 (d; H3); 7.7 (d, H8); 7.9 (d, H7), 8.5 (d; H5); 10.0 (d; H4); 12.4 (bs, NH).

EXAMPLE 3

Tetraethyl-{[(2-oxo-2H[1]-benzopyrano-3,6-di-yl)diamino]dimethylene}malonate

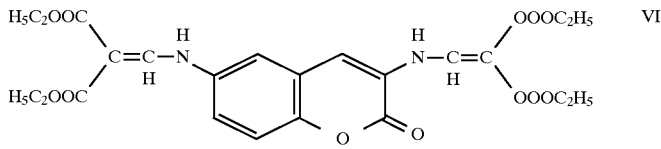

It was prepared according to the method described in Example 2 starting from 3,6-diaminocoumarin (1.00 g, 5.676 mmole) and diethyl-etoxymethylene malonate (2.81 g, 0.013 mole). Reaction duration: 6 hours. Recrystallization from ethanol gave yellow-green crystals of tetraethyl-{[(2-oxo-2H[1]-benzopyrano-3,6-di-yl)diamino]-dimethylene}malonate (2.55 g, 87%). M.p.: 131°–134° C.

Analysis:

calculated for $C_{25}H_{28}N_2O_{10}$: C=58.13; H=5.46; N=5.43. found: C=57.74; H=5.19; N=5.40.

$^1$H-NMR (DMSO-$d_6$). δ/ppm: 1.2 (t, $CH_3$), 4.2 (q, $CH_2$); 7.4 (m, C H), 7.6 (s, H5); 7.9 (s, H4); 8.2–8.5 (m; H7–H8); 10.6–10.8 (m; 2NH).

EXAMPLE 4

Diethyl-{[(3-hydroxy-2-oxo-2H[1]-benzopyrano-6-yl)amino]methylene}malonate

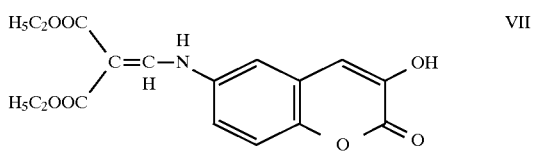

It was prepared according to the method described in Example 2 starting from 6-amino-3-hydroxycoumarin (0.88 g, 4.967 mmole). Reaction duration: 1 hour. The yellow-brown precipitate of diethyl-{[(3-hydroxy-2-oxo-2H[1]-benzopyrano-6-yl)-amino]methylene}malonate obtained by cooling the solution was recrystallized from glacial acetic acid (1.52 g, 88%).

Analysis:

calculated for $C_{17}H_{17}NO_7$: C=58.79; H=4.93; N=4.03. found: C=58.64; H=4.64; N=4.25.

$^1$H-NMR (DMSO-$d_6$). δ/ppm: 1.3 (t, $CH_3$), 4.2 (q, $CH_2$); 7.1–8.4 (m; Ar H); 10.5 (s; NH); 10.8 (d; OH). m/z: 347 ($M^+$), 302, 149, 79, 61, 45, 43.

EXAMPLE 5

Diethyl-{[(3-hydroxy-2-oxo-2H[1]-benzopyrano-8-yl)amino]methylene}malonate

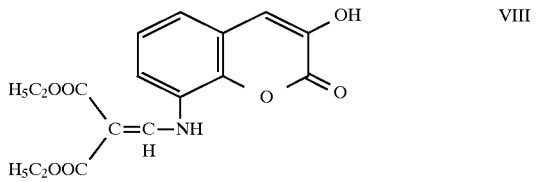

It was prepared according to the method described in Example 2 starting from 8-amino-3-hydroxycoumarin (1.93 g, 0.011 mole). Reaction duration: 4 hours. Recrystallization from glacial acetic acid gave a precipitate of diethyl-{[(3-hydroxy-2-oxo-2H[1]-benzopyrano-8-yl)amino] methylene}malonate in the form of brown shiny plate crystals (3.37 g, 89%).

Analysis:

calculated for $C_{17}H_{17}NO_7$: C=58.79; H=4.93; N=4.03. found: C=58.98; H=4.89; N=3.91.

$^1$H-NMR (DMSO-$d_6$). δ/ppm: 1.3 (t, $CH_3$), 4.2 (q, $CH_2$); 7.1–8.5 (m; Ar H); 10.7 (s; NH); 11.1 (d; OH). m/z: 347 ($M^+$), 302, 273, 199, 177, 70, 61, 47.

EXAMPLE 6

Diethyl-{[(8-fluoro-2-oxo-2H[1]-benzopyrano-3-yl)amino]methylene}malonate

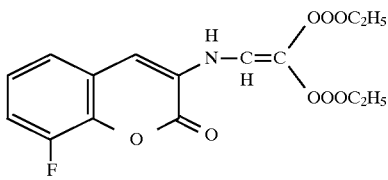

It was prepared according to the method described in Example 2 starting from 3-amino-8-fluorocoumarin (2.00 g, 9.250 mmole). Reaction duration: 5 hours. Cooling of the solution gave the precipitate of light yellow diethyl-{[(8-fluoro-2-oxo-2H[1]-benzo-pyrano-3-yl)amino] methylene}malonate, which was recrystallized from ethanol (2.76 g, 95%). M.p.: 175°–177° C.

Analysis:

calculated for $C_{17}H_{16}FNO_6$: C=58.45; H=4.62; N=4.01. found: C=58.38 H=4.46; N=3.98.

Example 7

Diethyl-{[(4-methyl-2-oxo-2H[1]-benzopyrano-7-yl)amino]methylene}malonate

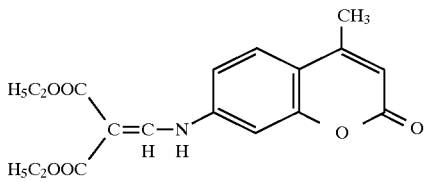

It was prepared according to the method described in Example 2 starting from 7-amino-4-methylcoumarin (5.00 g, 0.029 mole). Reaction duration: 30 minutes. The precipitated diethyl-{[(4-methyl-2-oxo-2H[1]-benzopyrano-7-yl)amino]methylene}malonate was recrystallized from ethanol (9.70 g, 98%). M.p.: 139°–140° C.

Analysis:

calculated for $C_{18}H_{19}NO_6$: C=62.60; H=5.55; N=4.06. found: C=61.97 H=5.05; N=4.25.

EXAMPLE 8

Diethyl-{[(4(trifluoromethyl)-2-oxo-2H[1]-benzopyrano-7-yl)amino]methylene}malonate

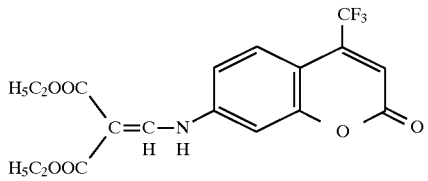

It was prepared according to the method described in Example 2 starting from 7-amino-4-trifluoromethyl) coumarin (3.00 g, 0.015 mole). Reaction duration: 27 hours. By cooling yellow diethyl-{[(4-trifluoromethyl-2-oxo-2H[1]-benzopyrano-7 -yl)-amino]methylene}malonate was precipitated, which was recrystallized from ethanol (4.83 g, 92%). M.p.: 125°–126° C.

Analysis:

calculated for $C_{18}H_{16}F_3NO_6$: C=54.14; H=4.04; N=3.51. found: C=54.12 H=4.17; N=3.46.

$^1$H-NMR (DMSO-d$_6$). δ/ppm: 1.3 (t; CH$_3$); 4.2 (q; CH$_2$); 6.8 (s, H3), 7.4–7.6 (m; H6, H8, C H); 8.4 (d, H5); 10.7 (d; NH).

We claim:

1. Coumarin derivative of the formula I

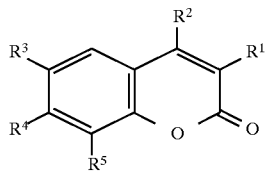

wherein $R^1$=NH$_2$ or —NHCH=C(CO$_2$C$_2$H$_5$)$_2$, $R^2$=$R^3$=$R^4$=H, $R^5$=F, $R^1$=$R^3$=NHCH=C(CO$_2$C$_2$H$_5$)$_2$, $R^2$=$R^4$=$R^5$=H, $R^1$=OH, $R^3$=NHCH=C(CO$_2$C$_2$H$_5$)$_2$, $R^2$=$R^4$=$R^5$=H, $R^1$=OH, $R^2$=$R^3$=$R^4$=H, $R^5$=—NHCH=C(CO$_2$C$_2$H$_5$)$_2$, or $R^1$=$R^3$=$R^5$=H, $R^2$=CH$_3$ or CF$_3$, $R^4$=—NHCH=C(CO$_2$C$_2$H$_5$)$_2$.

2. Coumarin derivative of the formula I of claim 1, characterized in that $R^1$=NH$_2$, $R^2$=$R^3$=$R^4$=H, $R^5$=F.

3. Coumarin derivative of the formula I of claim 1, characterized in that $R^2$=$R^4$=$R^5$=H, $R^1$=$R^3$=—NHCH=C(CO$_2$C$_2$H$_5$)$_2$.

4. Coumarin derivative of the formula I of claim 1, characterized in that $R^1$=OH, $R^3$=—NHCH=C(CO$_2$C$_2$H$_5$)$_2$, $R^2$=$R^4$=$R^5$=H.

5. Coumarin derivative of the formula I of claim 1, characterized in that $R^1$=OH, $R^2$=$R^3$=$R^4$=H, $R^5$=—NHCH=C(CO$_2$C$_2$H$_5$)$_2$.

6. Coumarin derivative of the formula I of claim 1, characterized in that $R^1$=—NHCH =C(CO$_2$C$_2$H$_5$)$_2$, $R^2$=$R^3$=$R^4$=H, $R^5$=F.

7. Coumarin derivative of the formula I of claim 1, characterized in that $R^1$=$R^3$=$R^5$=H, $R^2$=CH$_3$, $R^4$=—NHCH=C(CO$_2$C$_2$H$_5$)$_2$.

8. Coumarin derivative of the formula I of claim 1, characterized in that $R^1$=$R^3$=$R^5$=H, $R^2$=CF$_3$, $R^4$=—NHCH=C(CO$_2$C$_2$H$_5$)$_2$.

9. A process for the preparation of a compound of the formula I of claim 1, characterized in that a compound of the formula II

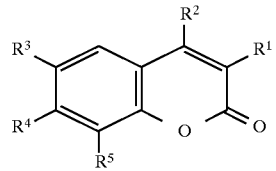

wherein $R^1$=$R^3$=$R^4$=$R^5$=H, $R^2$=NH$_2$, $R^1$=$R^3$=NH$_2$, $R^2$=$R^4$=$R^5$==H, $R^1$=OH, $R^2$=$R^4$=$R^5$=H, $R^3$=NH$_2$, $R^1$=OH, $R^2$=$R^3$=$R^4$=H, $R^5$=NH$_2$, $R^1$=NH$_2$, $R^2$=$R^3$=$R^4$=H, $R^5$=F, or $R^1$=$R^3$=$R^5$=H, $R^2$=CH$_3$ or CF$_3$, $R^4$=NH$_2$, and diethyl-ethoxymethylene malonate of the formula III

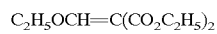

are heated at the temperature of 120° C. within a period from 10 minutes to 27 hours, followed by cooling, whereat coumarin malonate esters are precipitated.

* * * * *